(12) United States Patent
Gong et al.

(10) Patent No.: US 10,569,273 B2
(45) Date of Patent: Feb. 25, 2020

(54) RAPID THERMAL CYCLING FOR SAMPLE ANALYSES AND PROCESSING

(71) Applicant: STAR ARRAY PTE LTD, Singapore (SG)

(72) Inventors: Haiqing Gong, Singapore (SG); Yan Wen, Singapore (SG); Xudong Zeng, Singapore (SG)

(73) Assignee: STAR ARRAY PTE LTD, Singapore (SG)

( * ) Notice: Subject to any disclaimer, the term of this patent is extended or adjusted under 35 U.S.C. 154(b) by 0 days.

(21) Appl. No.: 16/199,261

(22) Filed: Nov. 26, 2018

(65) Prior Publication Data

US 2019/0091694 A1    Mar. 28, 2019

Related U.S. Application Data

(63) Continuation-in-part of application No. PCT/SG2017/050288, filed on Jun. 7, 2017.

(Continued)

(30) Foreign Application Priority Data

Jan. 12, 2017   (SG) .............................. 10201700260

(51) Int. Cl.
  *B01L 7/00*    (2006.01)
  *B01L 7/02*    (2006.01)
  (Continued)

(52) U.S. Cl.
  CPC ......... *B01L 7/5255* (2013.01); *B01F 11/0005* (2013.01); *B01L 3/5027* (2013.01); *B01L 7/02* (2013.01); *B01L 7/52* (2013.01); *B01L 9/00* (2013.01); *B01L 9/06* (2013.01); *C12Q 1/686* (2013.01); *C12Q 1/6848* (2013.01);
  (Continued)

(58) Field of Classification Search
  CPC ........ B01L 7/5255; B01L 7/02; B01L 3/5027; B01L 2200/06; B01L 2300/185; B01L 2300/1894; B01L 2300/0627; C12Q 1/686
  See application file for complete search history.

(56) References Cited

U.S. PATENT DOCUMENTS 9,794,986 B2 *   10/2017   Jarvis ..................... A01N 25/34

FOREIGN PATENT DOCUMENTS

| WO | 2010030647 A1 | 3/2010 | |
|---|---|---|---|
| WO | 2013177429 A2 | 11/2013 | |
| WO | WO-2013177429 A2 * | 11/2013 | ............. C12Q 1/686 |

* cited by examiner

*Primary Examiner* — Michael L Hobbs
(74) *Attorney, Agent, or Firm* — Bayramoglu Law Offices LLC (57) ABSTRACT

A method and an apparatus for thermal processing of nucleic acid in a thermal profile. The method employs at least a first bath and a second bath, the method further employing a reactor holder for holding reactor(s) accommodating reaction material containing the nucleic acid. The method includes maintaining bath mediums in the baths at two different temperatures; and alternately allowing the reactor(s) to be in the two baths in a plurality of thermal cycles to alternately attain a predetermined high target temperature $T_{HT}$, and a predetermined low target temperature $T_{LT}$, wherein the bath medium in at least one of the baths is a high thermal conductivity powder.

23 Claims, 6 Drawing Sheets

Related U.S. Application Data (60) Provisional application No. 62/348,155, filed on Jun. 10, 2016.

(51) Int. Cl.

| | | |
|---|---|---|
| *B01L 9/06* | (2006.01) | |
| *B01F 11/00* | (2006.01) | |
| *C12Q 1/686* | (2018.01) | |
| *G01N 35/04* | (2006.01) | |
| *B01L 3/00* | (2006.01) | |
| *B01L 9/00* | (2006.01) | |
| *C12Q 1/6848* | (2018.01) | |
| *G01N 35/00* | (2006.01) | |

(52) U.S. Cl.
CPC ....... *G01N 35/00584* (2013.01); *G01N 35/04* (2013.01); *B01L 3/5082* (2013.01); *B01L 2200/025* (2013.01); *B01L 2200/06* (2013.01); *B01L 2200/14* (2013.01); *B01L 2300/0618* (2013.01); *B01L 2300/0627* (2013.01); *B01L 2300/0816* (2013.01); *B01L 2300/0829* (2013.01); *B01L 2300/0832* (2013.01); *B01L 2300/0858* (2013.01); *B01L 2300/185* (2013.01); *B01L 2300/1805* (2013.01); *B01L 2300/1827* (2013.01); *B01L 2300/1894* (2013.01); *B01L 2400/065* (2013.01); *G01N 2035/00366* (2013.01); *G01N 2035/00386* (2013.01); *G01N 2035/00396* (2013.01); *G01N 2035/0412* (2013.01)

RAPID THERMAL CYCLING FOR SAMPLE ANALYSES AND PROCESSING

CROSS REFERENCE TO THE RELATED APPLICATIONS

The present application is continuous in part application of the International Patent Application No: PCT/SG2017/050288 filed on 7 Jun. 2017, which claims priority to U.S. Patent Application No. 62/348,155 filed on 10 Jun. 2016 and SG Patent Application No. 10201700260X filed on 12 Jan. 2017, the entire contents of which are incorporated herein by reference.

TECHNICAL FIELD

The present invention relates to a method and an apparatus for performing amplification reaction of nucleic acids in a sample.

BACKGROUND

Polymerase chain reaction (PCR) is increasingly important to molecular biology, food safety and environmental monitoring. A large number of biological researchers use PCR in their work on nucleic acid analyses, due to its high sensitivity and specificity. The time cycle of a PCR is typically in the order of an hour, primarily due to a time-consuming PCR thermal cycling process that is adapted to heat and cool reactors containing the sample to different temperatures for DNA denaturation, annealing and extension. Typically, the thermal cycling apparatus and method employs moving the reactors between two heating baths whose temperatures are set at the target temperatures as required for nucleic acid amplification reactions. Researchers have been constantly striving to increase the speed of thermal cycling.

Thermoelectric cooler (TEC) or Peltier cooler is also used as the heating/cooling element. However, it provides a typical ramping rate of 1-5 degree C./sec which is rather slow in changing the temperature of the reactor and disadvantageously increases the time of the thermal cycling.

As an attempt to increase the PCR speed by reducing thermal mass, microfabricated PCR reactor with embedded thin film heater and sensor was developed to achieve faster thermal cycling at a cooling rate of 74 degree Celsius/s and a heating rate of around 60-90 degree Celsius/s. However, such a wafer fabrication process for making the PCR device is extremely expensive and thus is impractical in meeting the requirement of low cost disposable applications in biological testing.

Hot and cold air alternately flushing the reactors in a closed chamber to achieve higher temperature ramping than the TEC-based thermal cycler has been described. However, from the heat transfer point of view, air has much lower thermal conductivity and heat capacity than liquid, hence the temperature ramping of the air cycler is slower than that with a liquid. The TEC needs a significant amount of time to heat and cool itself and the heat block above the TEC. Further there is also need to overcome the contact thermal resistance between the heat block and the reactors.

Alternating water flushing cyclers were also developed in which water of two different temperatures alternately flush the reactors to achieve PCR speed. However, such devices contain many pumps, valves and tubing connectors which increase the complexity of maintenance and lower the reliability while dealing with high temperature and high pressure. With circulating liquid bath medium, the liquid commonly spills out from the baths.

Traditional water bath PCR cyclers utilize the high thermal conductivity and heat capacity of water to achieve efficient temperature heating and cooling. But, such cyclers have large heating baths containing a large volume of water which is hard to manage in loading and disposal, and also makes the heating time to target temperatures too long before thermal cycling can start. Such cyclers also have large device weight and high power consumption. The water tends to vaporize with usage and needs to be topped up. Besides, during the thermal cycling every time the reactor is alternately inserted into the baths, a layer of water remains adhered on the reactor body when taken out of each bath, thereby causing the change in temperature inside the reactor to get slower undesirably.

Researchers also tested moving heated rollers of different temperatures to alternately contact the reactors. However, use of long tubing reactors make it not only cumbersome to install and operate a large array of reactors, but also expensive. When the reactors are in a large array or a panel, it may be challenging to achieve heating uniformity among all the reactors.

The present invention provides an improved method and apparatus for enabling the PCR at an ultra-fast speed at affordable cost without using complex and expensive components or consumables. The apparatus is robust, light weight, easy to use, needs a small amount of bath medium in the baths and can handle disposable reactors for the reaction material to avoid cross contamination from one reactor to the next. This invention provides a great positive impact on biological analysis.

SUMMARY

Unless specified otherwise, the term "comprising" and "comprise" and grammatical variants thereof, are intended to represent "open" or "inclusive" language such that they include recited elements but also permit inclusion of additional, unrecited elements. The word "substantially" does not exclude completely. The terminologies 'first bath', 'second bath' . . . 'sixth bath' do not constitute the corresponding number of baths in a sequence but merely are names for ease of identification with respect to the purpose they serve. These baths may not represent separate physical entities as some of them may be sharable. The term 'thermal processing' includes: a) thermal cycling, and optionally includes: b) thermal process steps before and/or after thermal cycling. The term 'thermal profile' refers to the temperature-time variation of the reactor(s) during a) alone or during a) with b).

According to a first aspect, a method is provided for thermally processing nucleic acid in a thermal profile, the method employing at least a first bath and a second bath, bath mediums in the baths being respectively maintainable at two different temperatures, the method further employing a reactor holder for holding reactor(s) each accommodating reaction material containing the nucleic acid and the reactor(s) being in any form such as tubes or wellplates or chips or cartridges, the method comprising alternately allowing the reactor(s) to be in the two baths in a plurality of thermal cycles to alternately attain a predetermined high target temperature THT, and a predetermined low target temperature TLT, wherein the bath medium in at least one of the baths is a high thermal conductivity powder. With respect to a liquid bath medium, the high thermal conductivity powder enhances the conductive heat transfer to the reactor(s), homogenizes the temperature field inside a bath and improves temperature uniformity along the reactors. The initial heating time of the baths to the predetermined temperatures is also significantly reduced. The powder also eliminates the issue of liquid adhesion to the surfaces of the reactors when the reactors move between the baths, thereby causing undesirable drifts in the temperatures of the baths and their calibrations. Such liquid adhesion also undesirably causes the reactors to retain the bath temperature for a duration even after being taken out of the bath. This can be avoided with the powder. The undesirable splashes when the reactor(s) are inserted in the liquid bath mediums are significantly reduced with the powder. Besides, the powder does not vaporize with time or usage, thereby require no refill as in the case of liquids.

According to an advantageous embodiment, the method comprises: in the first bath, allowing the reactor(s) to attain the THT, wherein the THT is in the region 85-99 degree Celsius for pre-denaturation and denaturation of the nucleic acid; and in the second bath, allowing the reactor(s) to attain the TLT, wherein the TLT is in the region 45-75 degree Celsius for annealing of primers or probes onto nucleic acid or for primer extension, the first and the second baths being for thermal cycling the reactor(s) to attain polymerase chain reaction (PCR) amplification or primer extension.

According to an advantageous embodiment, the method further employs a third bath, the method comprising: during thermal cycling, maintaining bath medium in the third bath at a medium temperature; and allowing the reactor(s) to be in the third bath to attain a predetermined medium target temperature TMT corresponding to the extension of primers in nucleic acid or the annealing of primers or probes onto nucleic acid. The method may further employ a fourth bath, the method comprising: before the thermal cycling, allowing the reactor(s) to be in the fourth bath to allow an additional process for the reactor(s) from the group consisting: reverse transcription-polymerase chain reaction (RT-PCR), hot start process, and isothermal amplification reaction. The third and/or the fourth baths advantageously allow the flexibility to attain various thermal profiles, depending on the type of the reaction material and the process of analysis. The bath mediums in the third and fourth baths may also be a high thermal conductivity powder for the advantages described under the first aspect. The method may also comprise allowing the reactor(s) to be in an air zone during the thermal cycling for conducting fluorescence imaging or electrochemical detection of the nucleic acid. The air zone provides a transparent medium for the optical imaging process which is otherwise not provided by the baths with the powder. In an alternate embodiment, the method comprises: employing a first optical fiber means for light transmission from an illumination light source into the reaction material; and employing a second optical fiber means for light transmission from the reaction material to a photodetector. This feature is useful particularly when the reactor is made of a metal tubing and when the imaging needs to be conducted when the reactor is in the powder.

The high thermal conductivity powder may be metal powder or metal powder dispersed in a liquid such as oil or glycerol or water or any mixture thereof as it fills up the voids between the particulates in the powder and liquids have much higher thermal conductivity and heat capacity than air. The liquid also reduces the frictional resistance while receiving the reactors, though at the cost of the oil/glycerol adhering to the surfaces of the reactors when taken out of the baths. The powder may comprise metal particles of substantially spherical shape to lower the frictional resistance while receiving the reactors. The powder may advantageously be copper powder of particle size in the range of 1 μm-5 mm. Copper powder is known to have a very high thermal conductivity and the described particle size is found to have low frictional resistance for commercially available reactors with diameters 0.1 mm-5 mm. The particle sizes within the bath may vary so as to optimize between the ease of insertion of the reactor(s) and the rate of heat transfer.

According to an embodiment, the method comprises employing the reactor(s) when in the form of tubes or well plates, with at least one feature from the group consisting: a metallic layer at the bottom tip of the reactor(s), and the bottom tip of the reactor(s) being sharper with lesser cross-sectional area than the rest of the reactor(s), to reduce frictional resistance while the powder receives the reactor(s).

According to an embodiment, the method further comprises: after thermal cycling, allowing the reactor(s) to be progressively heated in a fifth bath; and conducting melt curve analysis during the progressive heating for a subsequent study after the thermal cycling.

Advantageously, the method may comprise: employing a reactor guard to partially confine the reactor(s) to prevent the reactor(s) from getting deformed or from breaking under resistive forces and the THT when the reactor(s) is/are received in the powder. Higher the compactness of the metal powder, desirably higher is the rate of the heat transfer but is at the cost of increasing the resistance.

According to an embodiment, the method further comprises attaining the target temperatures by a temperature guided motion controlling means (TeGMCM) that is operable based on the real-time temperature as sensed by a reactor temperature sensor during thermal cycling. This method provides thermal cycling with higher accuracy and needs no user calibration though is at a higher cost and complexity of the apparatus due to requirement of very fast temperature sampling and signal processing electronics, fast data communication with the reactor transfer mechanism, and very responsive mechanical motion components such as motors and actuators in the reactor transfer mechanism. In an alternate embodiment, the method further comprises attaining the target temperatures by a time guided motion controlling means (TiGMCM) that is operable based on the time-periods for which the reactor(s) is/are allowed to be in the baths. The method may further comprise calibrating the TiGMCM for the time-periods. This embodiment requires lower complexity of the apparatus as it operates by time-duration hence does not require highly responsive set-up though needs user calibration. The method may further comprise calibrating a transfer means to initiate lift-off the reactor(s) from the bath(s) when the reactor(s) reach a first lift-off temperature that is lower than the THT and a second lift-off temperature that is higher than the TLT, in order to compensate for operational electro-mechanical delays that unwantedly cause over heating or over cooling of the reactor(s).

According to a second aspect, apparatus claims corresponding to the method claims are provided. The apparatus may further comprise shaking means for shaking at least one from the group consisting: the bath(s), the reactor(s), and both a) and b), during reactor insertion in the bath(s) so that the length of the reactor segment being heated does not change and the resistance of insertion of the reactor(s) into the powder is reduced.

According to a third aspect, the reactor guard is provided comprising confining means to partially confine the reactor(s) to prevent the reactor(s) from getting deformed under resistive forces and the $T_{HT}$ when the reactor(s) is/are received in the bath medium comprising high thermal conductivity powder. The guard may be made up of materials comprising metal or glass or high temperature plastics or ceramics which have enough strength to easily pierce through the powder and make way for the reactor(s) to be received in the powder bath. The reactor guard may be an extension of the reactor holder for convenience of lesser complexity.

According to a fourth aspect, the reactor(s) when in the form of tubes or well plates is/are provided with at least one feature from the group consisting: a metallic layer at the bottom tip of the reactor, and the bottom tip of the reactor being sharper with lesser cross-sectional area than the rest of the reactor, to reduce frictional resistance while the high thermal conductivity powder receives the reactor(s).

The present invention also enables the entire process of PCR based nucleic analysis to be completed in a very short time duration of a few minutes, from bath heating preparation, to reactor thermocycling and fluorescence signal acquisition.

BRIEF DESCRIPTION OF THE DRAWINGS

In the following drawings, same reference numbers generally refer to the same parts throughout. The drawings are not to scale, instead the emphasis is on describing the concept.

DETAILED DESCRIPTION

The following description presents several preferred embodiments of the present invention in sufficient detail such that those skilled in the art can make and use the invention.

Figure 1:
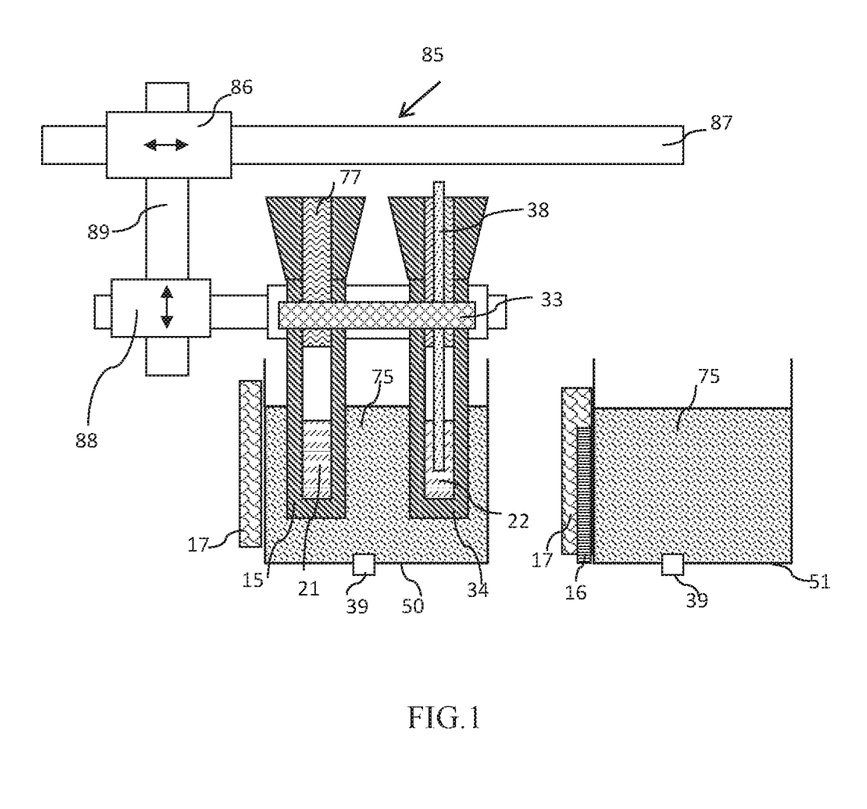
FIG. 1 is an schematic view of a set up for thermal cycling of a reaction material containing nucleic acid using copper powder as the bath medium, according to an embodiment of the invention.

FIG. 1 shows a schematic view of an embodiment of a portion of the thermal cycling apparatus for PCR or other enzymatic reactions to amplify nucleic acids or a fragment of nucleic acid. The apparatus has two baths 50 and 51 containing copper powder as the bath medium 75. Each bath 50 or 51 has a bath heater 17 and a bath temperature sensor 39 mounted along the bath surface to enable control of the temperature of the bath medium 75. According to another embodiment, the bath temperature sensors 39 may be positioned inside the baths 50, 51. Bath 50 is set at a temperature that is suitable for the step of denaturation and the bath 51 is set at temperature that is suitable for the step of annealing and/or extension. The cooler 16 is useful when the bath 51 needs to be actively cooled to below room temperature. The copper powder bath medium 75 enables faster and more accurate ramp-up and ramp down of the temperatures of the reactor 15 than that achievable with liquid bath medium. For some embodiments, the bath heater 17 on the low temperature bath 51 is optional, if bath 51 does not have to be heated. For the thermal cycling, the reactor 15 is alternately transferred between the baths 50, 51 multiple times. To enable fast plunging of the reactor 15 into the bath medium 75, slim reactor 15 is preferable such as glass capillaries. The reactor 15 is sealed with a sealant or a cap 77 and a portion of the reactor 15 is transparent to allow light to pass through for dye or probe excitation and fluorescence imaging when the reactor is not in the copper powder bath medium 75. A temperature monitoring unit 34 is installed on the reactor holder 33 and moves along with the reactor 15 between the baths 50, 51. The temperature monitoring unit 34 contains a fast response temperature sensor 38 inside. The temperature monitoring unit 34 has a shape similar to that of the reactor 15 and is constructed to have a similar or the same steady state and transient thermal characteristics as those of the reactor 15, for the temperature reading and thermal response to be similar or same as those of the reactor 15 unless another reactor 15 itself is used for the purpose. For example, the temperature monitoring unit 34 may have the fast response temperature sensor 38 inserted into water or oil or a layer of oil over water 22 and sealed. Although only one reactor 15 is shown, according to other embodiments the reactor holder 33 may accommodate a plurality of reactors 15. The reactor 15 may be in the form of tube(s) as shown or as wellplate or chip(s) or cartridge(s). The reactor transfer mechanism 85 transfers the reactor 15 and the temperature monitoring unit 34 at high speed among the baths 50 and 51 to expose them alternately to the different temperatures in the baths 50 and 51 as required for the thermal cycling. There are many possible designs of the reactor transfer mechanism 85. One such mechanism is comprised of an X stage 86 moving along an X axis linear guide 87 for the reactor 15 and the temperature monitoring unit 34 to reach to a region above the baths 50 and 51, and a Z stage 88 moving along a Z axis linear guide 89 for the reactors 15 to move them down to enter the bath medium 75 or to be withdrawn from the bath medium 75. Such a transfer mechanism 85 can also consist of a rotary arm (not shown) that moves the reactor 15 and the temperature monitoring unit 34 in an angular direction along with the Z stage 88 moving along the Z axis linear guide 89. The reactors 15 have an opening for loading and retrieving reaction material 21 from inside, and the openings are sealable. The sealant 77 may be made of a silicone rubber or UV cured polymer, hot melt and/or wax and/or gel which is in solid phase during thermal cycling. The sealing can also be achieved using liquid such as oil, viscous polymer, and gel. The highly viscous liquid can be applied to the opening and/or top section of the reactors 15, it is able to block the vapor generated from the reaction material 21 from leaking out.

In another embodiment (not shown) of thermal cycling, in between the baths 50 and 51, the reactor 15 with the monitoring unit 34 may be inserted into a 3rd bath containing bath medium at a medium target temperature or positioned in hot air for a period of time required for annealing and or extension. Herein the thermal cycling is performed in three-steps by inserting the reactor 15 into the three baths within each thermal cycle.

According to yet another embodiment (not shown) a fourth bath is maintained at a predetermined temperature $T_{AP}$ and before the thermal cycling, the reactor 15 with the temperature monitoring unit 34 is inserted in the fourth bath to allow at least one additional process from the group consisting reverse transcription-polymerase chain reaction (RT-PCR) and isothermal amplification reaction. The RT-PCR is carried out prior to the thermal cycling for nucleic acid amplification.

A temperature guided motion controlling means (TeG-MCM) (not shown) may preferably be employed in the apparatus for allowing the reactor(s) 15 to remain in the bath(s) 50 to 54 until the corresponding target temperature is attained, in order to maintain better accuracy of the predetermined target temperatures attained by the reactor(s) 15. The TeGMCM may be provided with advance signals when the reactor(s) 15 are about to reach the target temperatures as sensed by the temperature monitoring unit 34 in order to avoid over heating or over cooling of the reactor(s) 15. The thermal cycling with this method provides higher accuracy and needs no user calibration though is at a higher cost and complexity of the apparatus due to requirement of very fast temperature sampling and signal processing electronics, fast data communication with the reactor transfer mechanism, and very responsive mechanical motion components such as motors and actuators in the reactor transfer mechanism. Alternately, a time guided motion controlling means (TiGMCM) may be used that is operable based on the time-periods for which the reactor(s) are allowed to be in the baths. The TiGMCM may be user calibrated for the time-periods. This embodiment requires lower complexity of the apparatus as it operates by time-duration hence does not require highly responsive set-up though needs user calibration.

Figure 2:
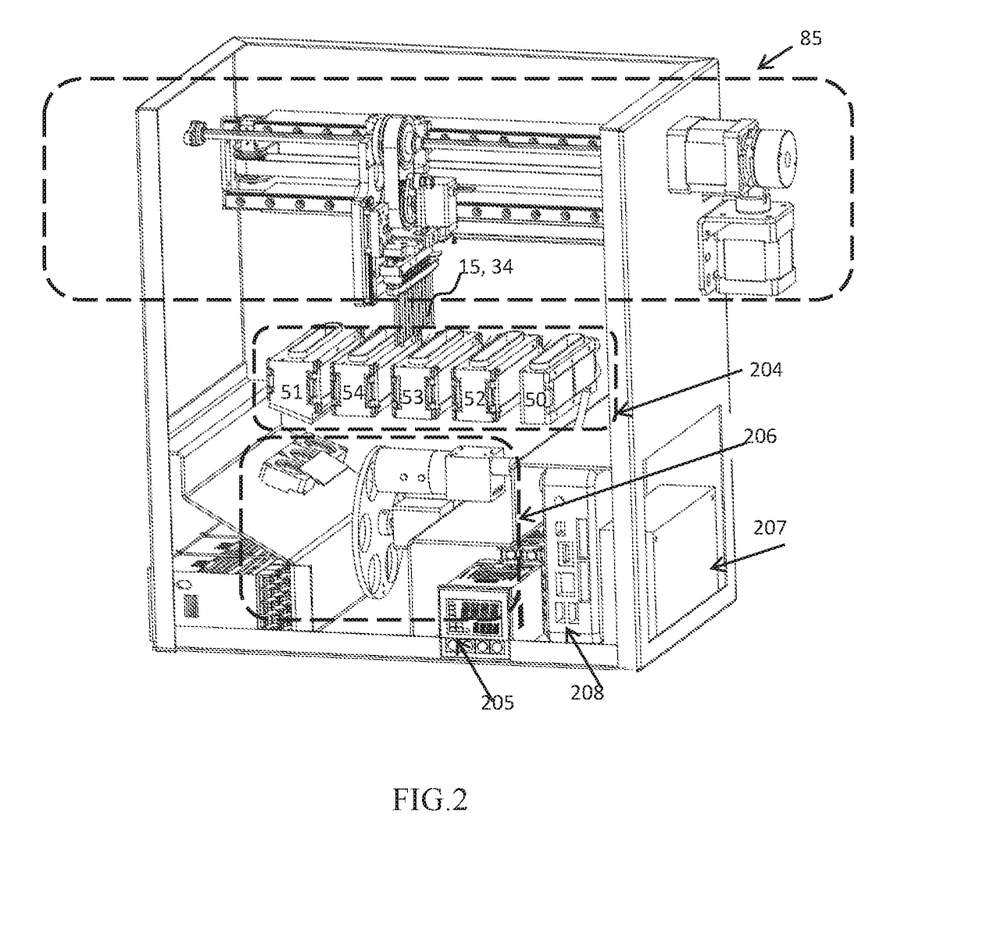
FIG. 2 is an isometric view of an embodiment of the apparatus for the process of thermal cycling as at FIG. 1.

FIG. 2 shows an isometric view of the apparatus with the reactor transfer mechanism 85, a bath module 204, an optical module 206, 205, 207 and 208. The bath module 204 is shown to comprise five baths 50, 51, 52, 53, 54 placed next to each other and each maintained at a predetermined temperature. An optics module 206 carries out fluorescent detection of nucleic acid inside the reactors 15 when the reactors 15 are situated in the low target temperature bath 51 having air or transparent liquid as the bath medium 75 in this embodiment. A temperature controller module 205 controls the bath temperatures. A motion controller module 207 controls all motions and a system controller module 208 controls the system, with data communication and processing, image processing and data analysis. The additional processes like reverse transcription-polymerase chain reaction (RT-PCR), hot start process, and isothermal amplification reaction can also be carried out in any of the baths for thermal cycling which can be set at the required temperature before the thermal cycling and reset to the temperature for thermal cycling after the completion of the above additional processes.

Figure 3:
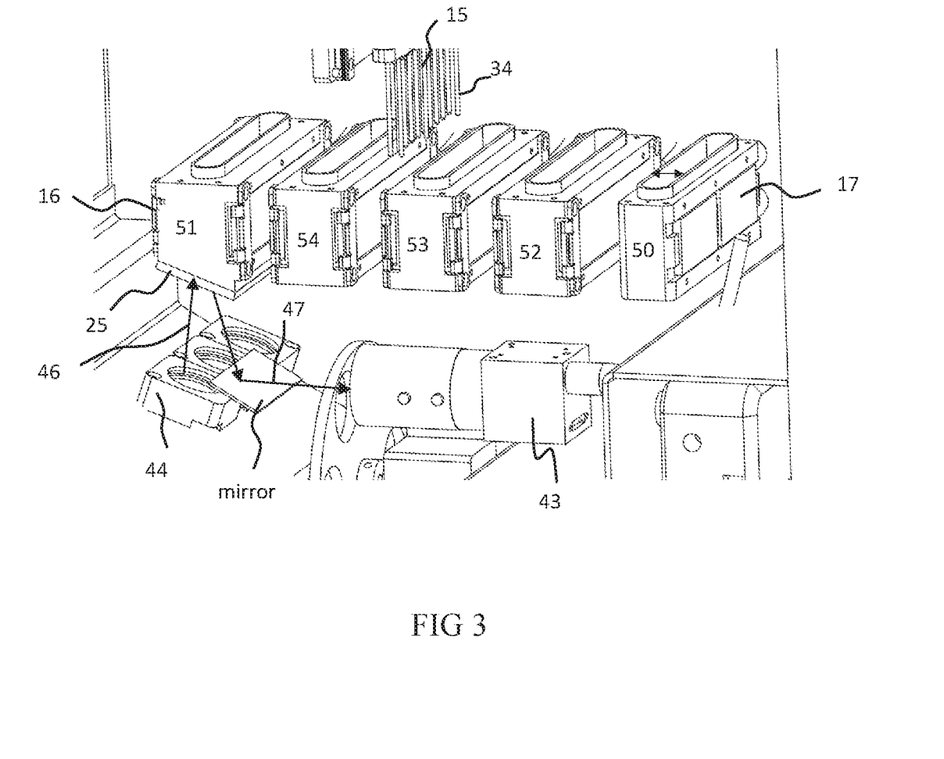
FIG. 3 is an isometric view of an embodiment of the reactor array and baths with optics modules of the apparatus in FIG. 2.

FIG. 3 shows a blown up illustration of the bath module 204 and the optical module 206. The optical module 206 comprises an illuminator 44 and a fluorescence detector 43. The incident beam 46 to reaches the reaction material 21 within the reactor 15. The reflected beam 47 from the reaction material 21 is captured thereafter. The array of reactors 15 with the temperature monitoring unit 34 are transferred among the baths 50 to 54. In this embodiment, the bath 51 has air or transparent liquid as the bath medium 75 along with a transparent window 25 at the bottom to pass the illumination light and emission light to and from the reactor 15. The bath heaters 17 or cooler 16 are connected to the sidewalls of the baths. The apparatus may may further comprise a hot air zone (not shown) for placing the reactors 15 particularly during imaging. This simplifies the apparatus. The method may employ an electrical heater or an infrared heater for forming the hot air zone above a bath or inside a bath. The heater may be installed with the reactor holder 33 so that only the air in the vicinity of the reactors 15 is heated while the reactor(s) 15 is/are moving between the baths. This feature saves energy and saves the other parts of the apparatus from getting undesirably heated.

Figure 4A:
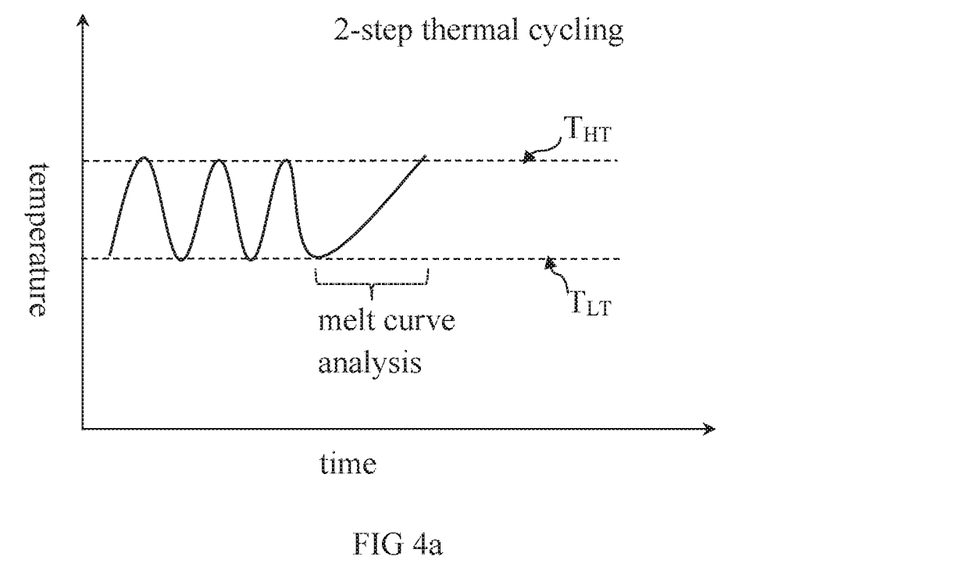
FIGS. 4a and 4b are exemplary graphical representations of typical 2-step and 3-step PCR processes along with melt curve analysis.
Figure 4B:
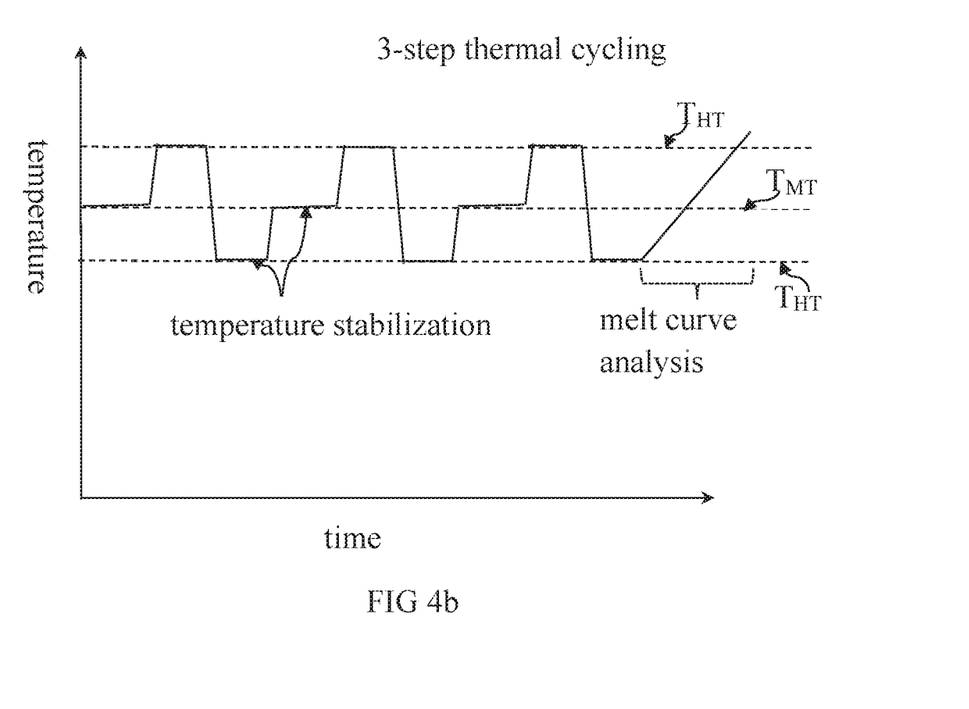

FIGS. 4a and 4b are exemplary time-temperature graphical representations of typical 2-step and 3-step thermal cycling processes (for PCR, primer extension and the kind), followed by a melt curve analysis. Only three cycles are shown over the processes of denaturation at the temperature $T_{HT}$ and annealing at the temperature $T_{LT}$ employing two baths in FIG. 4a and employing three baths in FIG. 4b for an additional step for extension at the temperature $T_{MT}$. After the thermal cycling, the reactors 15 are placed in at least a partially transparent bath medium that is progressively heated while melt curve analysis is conducted. The fluorescence signals from the reactors 15 are acquired at multiple temperatures to form a fluorescence-temperature curve for the melt curve analysis.

Figure 5:
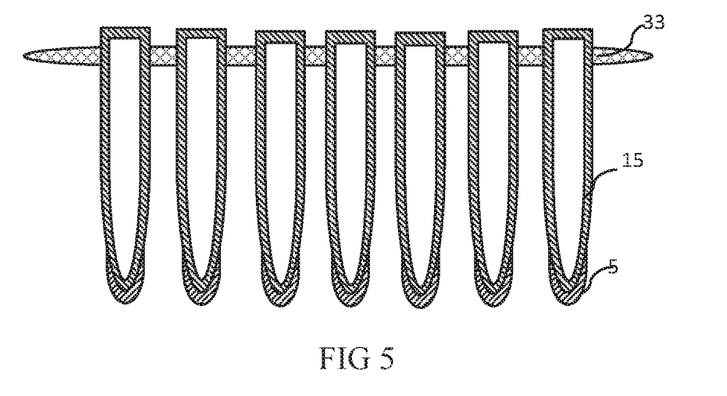
FIG. 5 is a cross-sectional diagram of an array of tubular reactors held by the reactor holder and with the bottom tips of the reactors being coated by a metallic layer as according to an embodiment of the invention.

FIG. 5 is a cross-sectional diagram of an array of tubular reactors 15 held by a reactor holder 33 and with the bottom tips of the reactors 15 being coated by a metallic layer 5 as according to an embodiment of the invention. When the bath medium 75 in at least one bath is metal powder, in order to enhance the insertion capability of the reactors 15 into the metal powder the reactors 15 are provided with metallic layer 5 at the bottom tips and the bottom tips are sharper with lesser cross-sectional area than the rest of the reactors 15.

Figure 6:
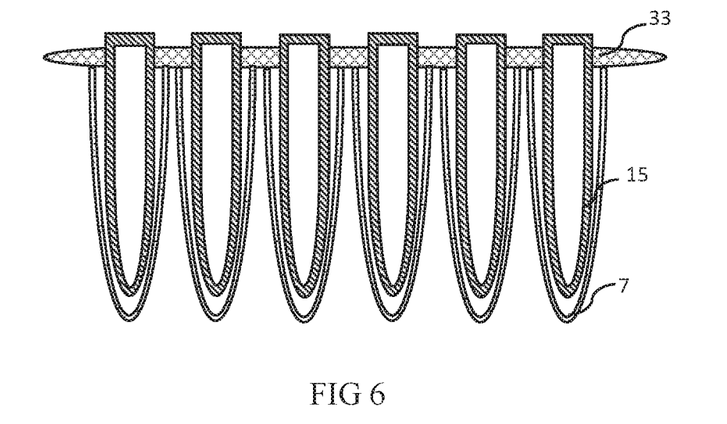
FIG. 6 is a cross-sectional diagram of an array of tubular reactors partially confined within reactor guards.
Figure 7:
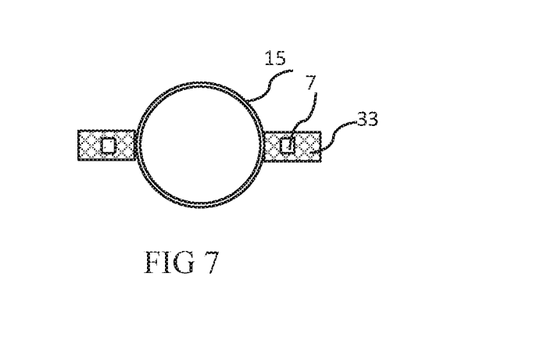
FIG. 7 is a top view of one reactor of FIG. 6, along with the reactor guard and reactor holder.

FIG. 6 is a cross-sectional diagram of an array of tubular reactors 15 partially confined within a reactor guard 7 that may be optionally used. The reactor guard 7 provides physical support to prevent the plastic reactors 15 from getting deformed under the resistive forces and the $T_{HT}$ or the glass reactors 15 from breaking under the resistive forces when the reactors 15 are inserted into the powder bath medium 75. Typically, such force is maximum on the reactor tip when the reactor 15 is inserted into the powder bath medium 75. The reactor guard 7 may be made up of materials comprising metal or glass or high temperature plastics or ceramics. FIG. 7 shows a top view of one reactor 15 with the reactor guard 7 and the reactor holder 33. As shown, the reactor guard 7 covers only a small portion of the reactors 15 hence does not obstruct fluorescent imaging.

Figure 8A:
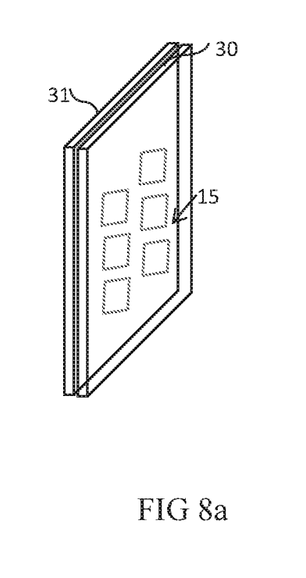
FIGS. 8a and 8b are perspective views of the reactors being accommodated in a biochip for use with the powder bath medium.
Figure 8B:
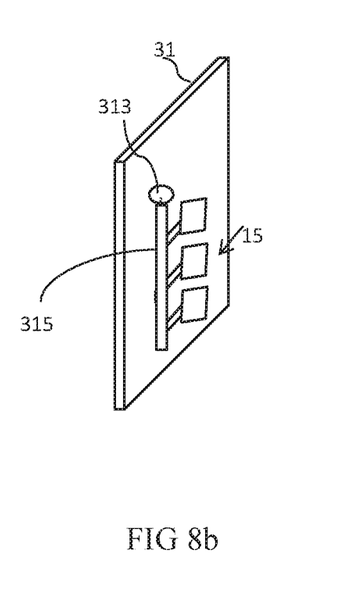

FIG. 8 (*a*) is a biochip 31 consisting of only reactors 15 in the form of wells with no channel 315. The reaction material 21 is dispensed from the opening of the reactors 15 and sealed by a cover or sealing fluid 30. Then, the biochip 31 is mounted onto the reactor holder 33. FIG. 8b is a perspective view of the reactors 15 being accommodated in a biochip 31 for use with the baths. Herein, a plurality of the reactors 15 are arranged in the biochip 31. The edges of the biochip 31 may be disposed with a material (not shown) that retains rigidity at high $T_{HT}$ and when used with the powder bath medium 75. There is at least one inlet 313 which is in fluid communication with the reactors 15 via a network of channels 315. The reaction material 21 to be tested can be loaded into the inlet 315 that subsequently flow into the reactors 15. For moving inside the powder bath medium 75.

Figure 9:
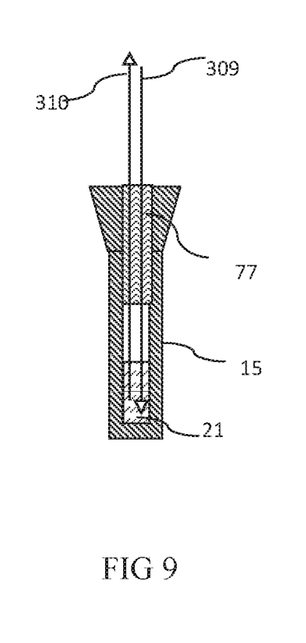
FIG. 9 is a cross-sectional view to illustrate the illumination and fluorescence emission detection module with an opaque tubular reactor that is particularly suited for powder bath medium as according to an embodiment.

FIG. 9 shows an embodiment where the reactor 15 is made of a metal tubing which is suitable for metal powder as the bath mediums 75. For the fluorescent imaging, an optical fiber 309 transmits light from an illumination light source such as an LED (not shown) into the reaction material 21 inside the reactor 15. Optical fiber 310 is for light transmission from the reaction material 21 to a photodetector (not shown). The sealant or cap 77 holds the optical fibers 309, 310. This facilitates the optical detection for the non-transparent reactor 15.

Figure 10:
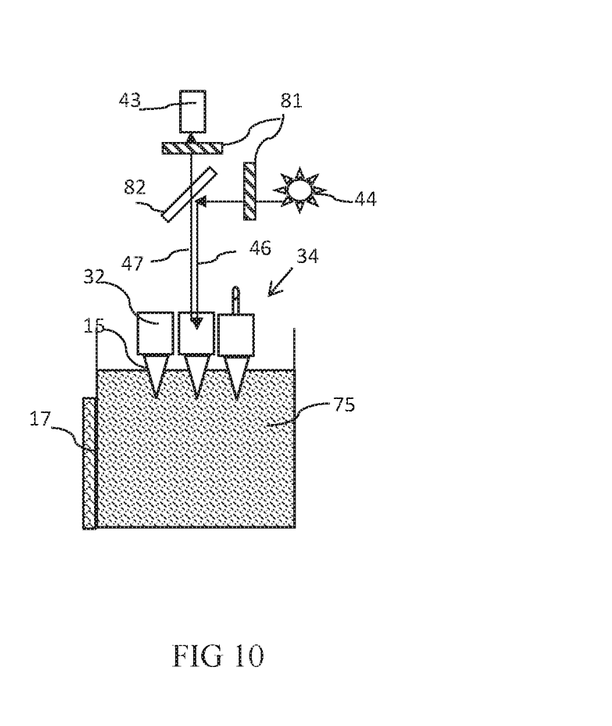
FIG. 10 is a side elevation view to illustrate the illumination and fluorescence emission detection module with a powder bath as according to an embodiment.

FIG. 10 is a side elevation view to illustrate the illumination and fluorescence emission detection module 206 with the opaque powder bath medium 75 as according to an embodiment. The optical module 206 comprises an illuminator 44, a fluorescence detector 43, optical filters 81 and a dichroic mirror 82 generate the incident beam 46 to reach the reaction material 21 within the reactor 15 and capture the reflected beam 47 from the reaction material 21 thereafter. The imaging mechanism is evident from the optical arrangement. Fluorescence imaging of the reactors 15 while the reactors 15 are inside the bath medium 75 is important since the reactors 15 may have to be maintained at the annealing or extension temperature for a prolonged period of time when multiple images of different wavelengths are taken for multiplex detection or to acquire fluorescence images of control genes. The reactor caps 32 are transparent to the lights for the imaging.

Different bath may contain different bath medium 75 for specific advantages as desired. The reactors 15 may be made up of plastics, elastomer, glass, metal, ceramic and their combinations, in which the plastics include polypropylene and polycarbonate. The glass reactor 15 can be made in a form of a glass capillary of small diameters such as 0.1 mm-3 mm OD and 0.02 mm-2 mm ID, and the metal can be aluminum in form of thin film, thin cavity, and capillary. Reactor materials can be made from non-biological active substances with chemical or biological stability. At least a portion of the reactor 15 is preferred to be transparent. In another embodiment, the reactors 15 can be in a form of a reactor array chip or a microfluidic reactor chip or arrayed chip. For example, the reactors 15 can be in a form of wells or channels of a substrate plate and optionally covered with a solid layer of material to form closed reaction chambers, in which the reaction fluid or reaction system is situated. The reaction material 21 in all the reactors 15 in the reactor holder 33 may not be identical. Simultaneous PCR can be advantageously conducted for different materials 21 if the bath temperatures are suitable. At least part of the reactor wall may be made of metal sheet of thickness 1 µm-2 mm. This feature enhances the rate of heat transfer between the bath and the reaction material 21. At least part of the reactor wall may be made of plastic or glass sheet of thickness 0.5 µm-500 µm. At least a part of the reactor wall is made of transparent material so as to enable the imaging and detection process. When using the above described apparatus for nucleic acid analysis and processing, the reaction material 21 comprises reaction constituents including at least one enzyme, nucleic acid and/or particle containing at least one nucleic acid, primers for PCR, primers for isothermal amplifications, primers for other nucleic acid amplifications and processing, dNTP, $Mg^{2+}$, fluorescent dyes and probes, control DNA, control RNA, control cells, control micro-organisms, and other reagents required for nucleic acid amplification, processing, and analysis. The particle containing nucleic acid mentioned above comprises at least one cell virus, white blood cell and stromal cell, circulating tumor cell, embryo cell. One application may be to use the apparatus to test different kinds of reaction materials 21 against the same set of primer and probes, such as test more than one sample. For such application, different kinds of reaction material 21 containing no target primers and/or probes are each loaded into one reactor 15 in a reactor array, with all the reactors 15 being pre-loaded with the same set or the same sets of PCR primers and/or probes. For the same application, different kinds of reaction materials 21 pre-mixed with respective PCR target primers and/or probes are each loaded into one reactor 15 in a reactor array, with all the reactors 15 being not pre-loaded with the same set of PCR primers and or probes. The reaction materials 21 can include control genes and/or cells and corresponding fluorescent dyes or probes. In the above situations, the different probes emit light of different wavelengths. Another application of the methods and devices are used to test the same reaction material 21 against different sets of primer and probes. One example of such an application is to test one type of sample for more than one purpose. For this application, a single reaction material 21 is added into the reactors 15 each loaded with at least one different set PCR primers and or probes. The reaction material 21 can include control genes and/or cells and corresponding fluorescent dyes or probes. In the above situations, the different probes emit light of different wavelengths. The above reaction material 21 is used in polymerase chain reaction, reverse transcription-PCR, end-point PCR, ligase chain reaction, pre-amplification or target enrichment of nucleic acid sequencing or variations of polymerase chain reaction (PCR), isothermal amplification, linear amplification, library preparations for sequencing, bridge amplification used in sequencing. The variation of the polymerase chain reaction mentioned above comprises reverse transcription-PCR, real-time fluorescent quantitative polymerase chain amplification reaction and real-time fluorescent quantitative reverse transcription polymerase chain amplification reaction, inverse polymerase chain amplification reaction, anchored polymerase chain amplification reaction, asymmetric polymerase chain amplification reaction, multiplex PCR, colour complementation polymerase chain amplification reaction, immune polymerase chain amplification reaction, nested polymerase chain amplification reaction, the target enrichment of pre-amplification or nucleic acid sequencing, ELISA-PCR The powder may be metallic like copper, or may be ceramic or glass or the powder may be dispersed in a liquid such as oil or glycerol or water or any mixture thereof. The liquid fills up the voids between the particles in the powder and liquids have much higher thermal conductivity and heat capacity than air. The liquid also reduces the frictional resistance to the movement of the reactors in the bath. The liquid however adheres to the surfaces of the reactors when taken out of the baths.

The particles in the powder may be of substantially spherical shape to lower the frictional resistance to the movement of the reactors in the bath. The powder may advantageously be of particle size in the range of 1 µm to 5 mm. A particle size of 0.1 to 1.0 mm may be optimum as finer particle sizes may cause health hazards upon inhalation and larger particle sizes tend to have more voids that deteriorate the heat transfer to the reactors.

Ceramic powder is known to have high thermal conductivity and the described particle size is found to have low frictional resistance for commercially available reactors with diameters 0.1 mm-5 mm. The particle sizes within the bath may be selected so as to optimize between the ease of insertion of the reactor(s) and the rate of heat transfer. Ceramic powder has the advantage of not oxidising with time unlike copper powder thereby reducing the thermal conductivity of the powder. Ceramic powder particles as manufactured have a shape that is more spherical than copper powder particles. Besides, the surface finish of ceramic particles is such that the inter-particle surface friction is much lower than that with metal particles. In the bath, these features of shape and surface finish advantageously reduce the frictional resistance to the movement of the reactors including glass capillaries.

Copper being electrically a good conductor, any spillage of the powder outside the baths may potentially cause short-circuits in the electrical components of the apparatus. Advantageously this is not the case with ceramic powder.

The powder described herein preferably has a thermal conductivity that is more than 0.3 watts per meter-kelvin (W/m·K), that is higher than the thermal conductivity of materials like plastics, wood or rubber. Higher the thermal conductivity of the powder, advantageously, lower is the duration of the thermal cycling.

From the foregoing description it will be understood by those skilled in the art that many variations or modifications in details of design, construction and operation may be made without departing from the present invention as defined in the claims.

What is claimed is:

1. A method of thermal cycling for polymerase chain reaction (PCR) of nucleic acid, the method employing at least a first bath and a second bath, the method further employing a reactor holder for holding reactor(s) accommodating reaction material containing the nucleic acid and the reactor(s) being in a form of capillaries or tubes or wellplates or chips or cartridges, the method comprising:
   maintaining bath mediums in the baths at two different temperatures; and
   alternately allowing the reactor(s) to be in the two baths in a plurality of thermal cycles to alternately attain:
   a predetermined high target temperature $T_{HT}$, and
   a predetermined low target temperature $T_{LT}$,
   wherein the bath medium in at least one of the baths is a powder,
   wherein the powder comprises particles of substantially spherical shape with a diameter of 0.1 mm-1 mm.

2. The method according to claim 1, further comprising maintaining the $T_{HT}$ in the region 85-99 degree Celsius for denaturation of the nucleic acid; and
   maintaining the $T_{LT}$ in the region 45-75 degree Celsius for annealing of primers or probes onto the nucleic acid or for primer extension.

3. The method according to claim 2, further comprising:
   allowing the reactor(s) to be in a third bath to attain a predetermined medium target temperature $T_{MT}$ corresponding to the extension of primers in the nucleic acid or the annealing of primers or probes onto the nucleic acid.

4. The method according to claim 1, further comprising:
   during the thermal cycling, allowing the reactor(s) to be in an air zone for conducting fluorescence imaging or electrochemical detection of the nucleic acid.

5. The method according to claim 1, further comprising:
   employing a first optical fiber means for light transmission from an illumination light source into the reaction material; and
   employing a second optical fiber means for light transmission from the reaction material to a photodetector.

6. The method according to claim 1, wherein
   the reactor(s) are in the form of tubes or well plates with a feature of
   a metallic layer at a bottom tip of the reactor(s).

7. The method according to claim 1, further comprising:
   attaining the target temperatures based on a real-time temperature as sensed by a reactor temperature sensor during thermal cycling.

8. The method according to claim 1, further comprising:
   attaining the target temperatures based on time-periods for which the reactor(s) are allowed to be in the baths.

9. An apparatus of thermal cycling for polymerase chain reaction (PCR) of nucleic acid, the apparatus employing a reactor holder for holding reactor(s) to accommodate reaction material containing the nucleic acid and the reactor(s) being in any form such as capillaries or tube(s) or wellplate(s) or chip(s) or cartridge(s), the apparatus comprising:
   a first bath;
   a second bath, bath mediums in the baths being respectively maintainable at two different temperatures, and
   a transfer means for allowing the reactor(s) to be in the two baths in a plurality of thermal cycles to alternately attain:
   a predetermined high target temperature $T_{HT}$, and
   a predetermined low target temperature $T_{LT}$; and
   an amount of powder to serve as the bath medium in at least one of the baths,
   wherein the powder comprises particles of substantially spherical shape with a diameter of 0.1 mm-1 mm.

10. The method according to claim 1, wherein the powder is selected from the group consisting of:
    i) ceramic powder,
    ii) glass powder,
    iii) metal powder,
    iv) copper powder,
    v) any of the above dispersed in a liquid, and
    vi) mixture of any of the above.

11. The method according to claim 1, wherein the powder has a thermal conductivity more than 0.3 watts per meter-kelvin (W/m·K).

12. The apparatus according to claim 9, wherein the powder is at least one selected from the group consisting of:
    i) ceramic powder,
    ii) glass powder,
    iii) metal powder, and
    iv) copper powder.

13. The apparatus according to claim 9, wherein the powder has a thermal conductivity that is more than 0.3 watts per meter-kelvin (W/mK).

14. The method according to claim 1, wherein the powder is ceramic powder.

15. The apparatus according to claim 9, wherein the powder is ceramic powder.

16. The apparatus according to claim 9, wherein the transfer means is further adapted to shaking the reactors when the reactors are inside at least one of the first bath or the second bath, the shaking being of a high speed reciprocating motion.

17. The apparatus according to claim 16, wherein the reciprocating motion is in a vertical direction or a depth direction of the first bath or the second bath.

18. The apparatus according to claim 16, wherein the reciprocating motion or the shaking is at a speed that is higher than 100 mm per second.

19. The apparatus according to claim 16, wherein the reciprocating motion or the shaking is at a speed that is higher than 500 mm per second.

20. A method of thermal cycling for polymerase chain reaction (PCR) of nucleic acid, the method employing at least a first bath and a second bath, the method further employing a reactor holder for holding reactor(s) accommodating reaction material containing the nucleic acid and the reactor(s) being in a form of capillaries or tubes or wellplates or chips or cartridges, the method comprising:
   maintaining bath mediums in the baths at two different temperatures; and
   alternately allowing the reactor(s) to be in the two baths in a plurality of thermal cycles to alternately attain:
   a predetermined high target temperature $T_{HT}$, and
   a predetermined low target temperature $T_{LT}$,
   wherein the bath medium in at least one of the baths is a powder
   and employing a reactor guard to partially confine the reactor(s) to prevent the reactor(s) from getting deformed under resistive forces of the bath medium and the $T_{HT}$ when the reactor(s) is/are received in the powder.

21. An apparatus of thermal cycling for polymerase chain reaction (PCR) of nucleic acid, the apparatus employing a reactor holder for holding reactor(s) to accommodate reaction material containing the nucleic acid and the reactor(s) being in any form such as capillaries or tube(s) or wellplate(s) or chip(s) or cartridge(s), the apparatus comprising:
   a first bath;
   a second bath, bath mediums in the baths being respectively maintainable at two different temperatures, and
   a transfer means for allowing the reactor(s) to be in the two baths in a plurality of thermal cycles to alternately attain:
   a predetermined high target temperature $T_{HT}$, and
   a predetermined low target temperature $T_{LT}$; and
   an amount of powder to serve as the bath medium in at least one of the baths
   and a reactor guard, wherein the reactor guard comprises a confining means to partially confine the reactor(s) to prevent the reactor(s) from getting deformed under resistive forces of the bath medium and the $T_{HT}$ when the reactor(s) is/are received in the bath medium comprising the powder.

22. The apparatus according to claim 21, wherein the reactor guard is made up of materials comprising metal or glass or high temperature plastics or ceramics.

23. The apparatus according to claim 21, wherein the reactor guard is an extension of the reactor holder.

* * * * *